US009289596B2

(12) United States Patent
Leven

(10) Patent No.: US 9,289,596 B2
(45) Date of Patent: Mar. 22, 2016

(54) LEADS WITH SEGMENTED ELECTRODES AND METHODS OF MAKING AND USING THE LEADS

(71) Applicant: BOSTON SCIENTIFIC NEUROMODULATION CORPORATION, Valencia, CA (US)

(72) Inventor: Jacob B. Leven, Huntington Beach, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 31 days.

(21) Appl. No.: 14/325,249

(22) Filed: Jul. 7, 2014

(65) Prior Publication Data
US 2015/0018915 A1 Jan. 15, 2015

Related U.S. Application Data

(60) Provisional application No. 61/845,739, filed on Jul. 12, 2013.

(51) Int. Cl.
*A61N 1/05* (2006.01)
*A61B 5/04* (2006.01)
(Continued)

(52) U.S. Cl.
CPC .............. *A61N 1/05* (2013.01); *A61N 1/0534* (2013.01); *A61B 5/04001* (2013.01);
(Continued)

(58) Field of Classification Search
CPC ..... A61N 1/05; A61N 1/0534; A61N 1/0551; Y10T 29/49204; Y10T 29/49222; Y10T 29/49218
See application file for complete search history.

(56) References Cited

U.S. PATENT DOCUMENTS

| 4,602,624 | A | 7/1986 | Naples et al. |
| 4,630,611 | A | 12/1986 | King |

(Continued)

FOREIGN PATENT DOCUMENTS

| EP | 0580928 A1 | 2/1994 |
| EP | 0650694 B1 | 7/1998 |

(Continued)

OTHER PUBLICATIONS

U.S. Appl. No. 14/286,889, filed May 23, 2014.
(Continued)

*Primary Examiner* — George Evanisko
(74) *Attorney, Agent, or Firm* — Lowe Graham Jones PLLC; Bruce E. Black

(57) ABSTRACT

A method of making a stimulation lead includes disposing a pre-electrode along a distal end portion of a lead body. The pre-electrode includes a body having a central hub and stimulation members individually coupled to the central hub and extending radially-outward therefrom such that each of the stimulation members is electrically-coupled to each of the remaining stimulation members solely via the central hub. Conductors extending from terminals disposed along a proximal end portion of the lead body are electrically-coupled to each of the stimulation members. Electrically-nonconductive material is disposed around longitudinal surfaces of the central hub with the electrically-nonconductive material abutting inner surfaces of the stimulation members. The central hub is removed from the pre-electrode body to electrically isolate each of the stimulation members from one another, thereby transforming the stimulation members into electrically-isolated segmented electrodes disposed along the electrically-nonconductive material.

11 Claims, 9 Drawing Sheets

(51) Int. Cl.
*A61M 25/00* (2006.01)
*A61M 25/01* (2006.01)

(52) U.S. Cl.
CPC .. *A61B 2562/0209* (2013.01); *A61B 2562/125* (2013.01); *A61M 25/0009* (2013.01); *A61M 25/0102* (2013.01); *A61N 1/0551* (2013.01); *Y10T 29/49176* (2015.01)

(56) References Cited

U.S. PATENT DOCUMENTS

| | | |
|---|---|---|
| 4,744,370 A | 5/1988 | Harris |
| 5,000,194 A | 3/1991 | van den Honert et al. |
| 5,135,001 A | 8/1992 | Sinofsky et al. |
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,824,030 A * | 10/1998 | Yang .............. A61N 1/056 600/374 |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,181,969 B1 | 1/2001 | Gord |
| 6,322,559 B1 | 11/2001 | Daulton et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,609,029 B1 | 8/2003 | Mann et al. |
| 6,609,032 B1 | 8/2003 | Woods et al. |
| 6,678,564 B2 | 1/2004 | Ketterl et al. |
| 6,741,892 B1 | 5/2004 | Meadows et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,203,548 B2 | 4/2007 | Whitehurst et al. |
| 7,244,150 B1 | 7/2007 | Brase et al. |
| 7,292,890 B2 | 11/2007 | Whitehurst et al. |
| 7,450,997 B1 | 11/2008 | Pianca et al. |
| 7,489,971 B1 | 2/2009 | Franz |
| 7,668,601 B2 | 2/2010 | Hegland et al. |
| 7,672,734 B2 | 3/2010 | Anderson et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,809,446 B2 | 10/2010 | Meadows |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,175,710 B2 | 5/2012 | He |
| 8,224,450 B2 | 7/2012 | Brase |
| 8,225,504 B2 | 7/2012 | Dye et al. |
| 8,271,094 B1 | 9/2012 | Moffitt et al. |
| 8,295,944 B2 | 10/2012 | Howard et al. |
| 8,321,025 B2 | 11/2012 | Bedenbaugh |
| 8,359,107 B2 | 1/2013 | Pianca et al. |
| 8,364,278 B2 | 1/2013 | Pianca et al. |
| 8,391,985 B2 | 3/2013 | McDonald |
| 8,583,237 B2 | 11/2013 | Bedenbaugh |
| 8,688,235 B1 | 4/2014 | Pianca et al. |
| 2001/0023368 A1 | 9/2001 | Black et al. |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0247697 A1 | 11/2006 | Sharma et al. |
| 2007/0150036 A1 | 6/2007 | Anderson |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0215125 A1 | 9/2008 | Farah et al. |
| 2008/0255647 A1 | 10/2008 | Jensen et al. |
| 2009/0187222 A1 | 7/2009 | Barker |
| 2009/0204192 A1 | 8/2009 | Carlton et al. |
| 2009/0276021 A1 | 11/2009 | Meadows et al. |
| 2010/0030298 A1 | 2/2010 | Martens et al. |
| 2010/0036468 A1 | 2/2010 | Decre et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |
| 2013/0105071 A1 | 5/2013 | DiGiore et al. |
| 2013/0109254 A1 | 5/2013 | Klardie et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |
| 2014/0039587 A1 | 2/2014 | Romero |
| 2014/0142671 A1 | 5/2014 | Moffitt et al. |
| 2014/0180375 A1 | 6/2014 | Pianca et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |

(56) References Cited

FOREIGN PATENT DOCUMENTS

| WO | 0038574 | A1 | 7/2000 |
| WO | 0158520 | A1 | 8/2001 |
| WO | 02068042 | A1 | 9/2002 |
| WO | 2004045707 | A1 | 6/2004 |
| WO | 2008018067 | A2 | 2/2008 |
| WO | 2008053789 | A1 | 5/2008 |
| WO | 2008/100841 | A1 | 8/2008 |
| WO | 2009025816 | A1 | 2/2009 |
| WO | 2009102536 | A1 | 8/2009 |
| WO | 2013162775 | A2 | 10/2013 |
| WO | 2014018092 | A1 | 1/2014 |

OTHER PUBLICATIONS

U.S. Appl. No. 14/286,934, filed May 23, 2014.
U.S. Appl. No. 14/286,829, filed May 23, 2014.
U.S. Appl. No. 14/286,940, filed May 23, 2014.
U.S. Appl. No. 14/332,212, filed Jul. 15, 2014.
U.S. Appl. No. 14/452,461, filed Aug. 5, 2014.
U.S. Appl. No. 14/286,797, filed May 23, 2014.
U.S. Appl. No. 14/469,214, filed Aug. 26, 2014.
International Search Report and Written Opinion for PCT/US2014/045618 mailed Sep. 26, 2014.
U.S. Appl. No. 14/557,211, filed Dec. 1, 2014.

* cited by examiner

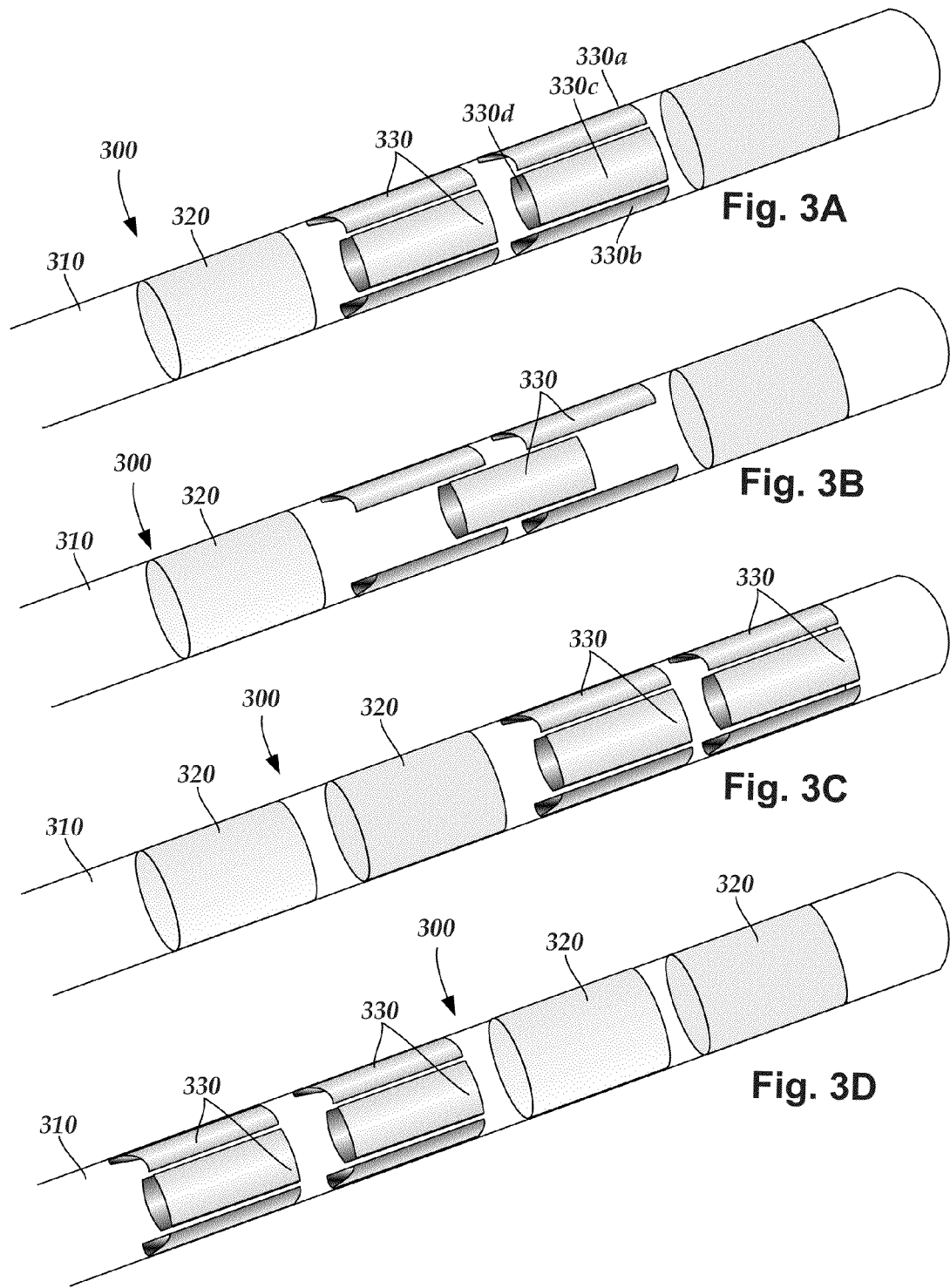

LEADS WITH SEGMENTED ELECTRODES AND METHODS OF MAKING AND USING THE LEADS

CROSS-REFERENCE TO RELATED APPLICATIONS

This application claims the benefit under 35 U.S.C. §119 (e) of U.S. Provisional Patent Application Ser. No. 61/845,739, filed Jul. 12, 2013, which is incorporated herein by reference.

FIELD

The invention is directed to the area of electrical stimulation systems and leads and methods of making and using the systems and leads. The present invention is also directed to electrical stimulation systems having leads with segmented electrodes that include removable central hubs, as well as methods of making and using the segmented electrodes, leads, and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

In one embodiment, a method of making a stimulation lead includes disposing at least one pre-electrode along a distal end portion of a lead body. The at least one pre-electrode includes a pre-electrode body having a proximal end and a distal end. The pre-electrode body includes an electrically-conductive central hub and electrically-conductive stimulation members individually coupled to the central hub and extending radially-outward therefrom such that each of the plurality of stimulation members is electrically-coupled to each of the remaining plurality of stimulation members solely via the central hub. At least one conductor of multiple conductors extending from terminals disposed along a proximal end portion of the lead body is electrically-coupled to each of the stimulation members. Electrically-nonconductive material is disposed around longitudinal surfaces of the central hub with the electrically-nonconductive material abutting inner surfaces of the plurality of stimulation members. The central hub is removed from the pre-electrode body to electrically isolate each of the stimulation members from one another, thereby transforming the stimulation members into electrically-isolated segmented electrodes disposed along the periphery of the electrically-nonconductive material.

In another embodiment, a pre-electrode for a stimulation lead includes a substantially-cylindrical pre-electrode body having a proximal end and a distal end. The pre-electrode body includes an electrically-conductive central hub having a longitudinal surface. The pre-electrode body also includes connector elements extending radially outward from the longitudinal surface of the central hub. The connector elements each have a medial end coupled to the central hub and an opposing lateral end. The pre-electrode body further includes stimulation members each having an inner surface and an outer surface. The inner surface of each of the stimulation members is coupled to the medial end of at least one of the connector elements such that each of the stimulation members is electrically-coupled to each of remaining stimulation members solely via the central hub.

In yet another embodiment, a stimulation lead includes a lead body having a longitudinal surface, a distal end portion, a proximal end portion, and a longitudinal length. A central lumen extends along the longitudinal length of lead body and is bounded by longitudinal walls. Insulating material is disposed at the distal end portion of the lead body between the lead body and the central lumen. Terminals are disposed along the proximal end portion of the lead body. Electrodes are disposed along the distal end portion of the lead body. The electrodes include segmented electrodes. Each of the segmented electrodes includes a stimulation member having an outer surface and an opposing inner surface; and a connector element coupled to the inner surface of the stimulation member and extending radially inward to the insulating material. Conductors electrically couple the terminals to the electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 3A is a perspective view of an embodiment of a portion of a lead having a plurality of segmented electrodes, according to the invention;

FIG. 3B is a perspective view of a second embodiment of a portion of a lead having a plurality of segmented electrodes, according to the invention;

FIG. 3C is a perspective view of a third embodiment of a portion of a lead having a plurality of segmented electrodes, according to the invention;

FIG. 3D is a perspective view of a fourth embodiment of a portion of a lead having a plurality of segmented electrodes, according to the invention;

DETAILED DESCRIPTION

The invention is directed to the area of electrical stimulation systems and leads and methods of making and using the systems and leads. The present invention is also directed to electrical stimulation systems having leads with segmented electrodes that include removable central hubs, as well as methods of making and using the segmented electrodes, leads, and electrical stimulation systems.

A lead for deep brain stimulation may include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes radially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves and tissues.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; and 8,391,985; U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and U.S. patent application Ser. Nos. 12/177,823; 13/667,953; and 13/750,725, all of which are incorporated by reference.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead may include both recording electrodes and stimulation electrodes or electrodes may be used for both recording and stimulation.

Figure 1:
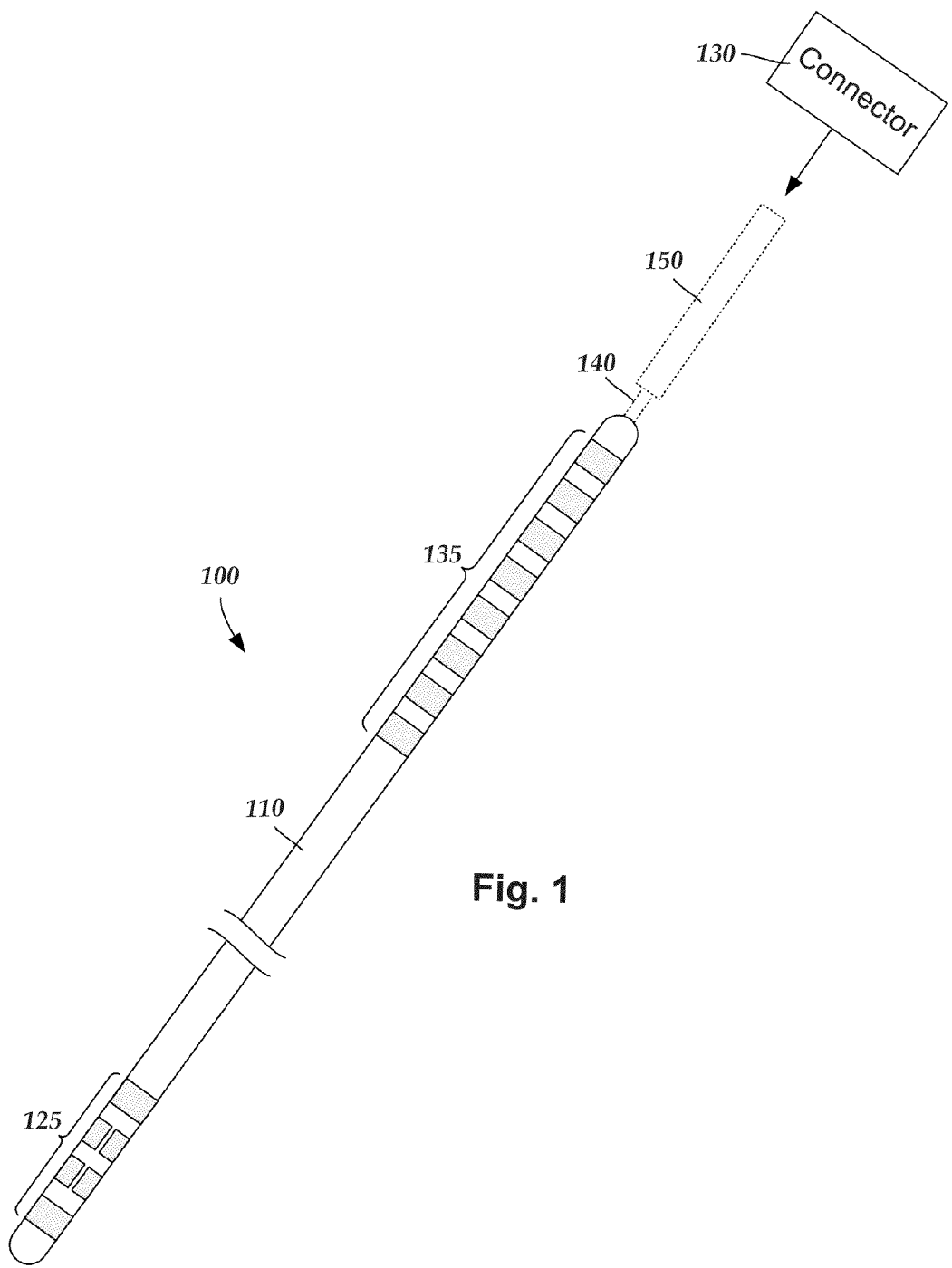
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 132 for connection of the electrodes to a control unit, and a stylet 140 for assisting in insertion and positioning of the lead in the patient's brain. In at least some embodiments, the stylet 140 is insertable into a stylet lumen (not shown) extending along a longitudinal length of the lead 110. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 132 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator may have more or fewer than eight stimulation channels (e.g., 4-, 6-, 16-, 32-, or more stimulation channels). The control unit may have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes typically do not enable stimulus current to be directed from only a limited angular range around of the lead. Segmented electrodes, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

The lead 100 includes a lead body 110, one or more optional ring electrodes 120, and a plurality of sets of segmented electrodes 130. The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes may be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Figure 3E:
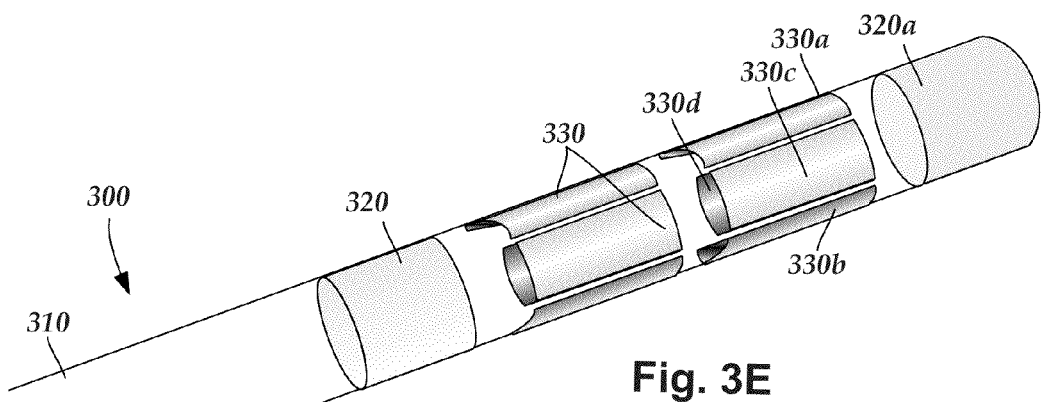
FIG. 3E is a perspective view of a fifth embodiment of a portion of a lead having a plurality of segmented electrodes, according to the invention.

Stimulation electrodes in the form of ring electrodes 120 may be disposed on any part of the lead body 110, usually near a distal end of the lead 100. In FIG. 1, the lead 100 includes two ring electrodes 120. Any number of ring electrodes 120 may be disposed along the length of the lead body 110 including, for example, one, two three, four, five, six, seven, eight, nine, ten, eleven, twelve, thirteen, fourteen, fifteen, sixteen or more ring electrodes 120. It will be understood that any number of ring electrodes may be disposed along the length of the lead body 110. In some embodiments, the ring electrodes 120 are substantially cylindrical and wrap around the entire circumference of the lead body 110. In some embodiments, the outer diameters of the ring electrodes 120 are substantially equal to the outer diameter of the lead body 110. The length of the ring electrodes 120 may vary according to the desired treatment and the location of the target neurons. In some embodiments the length of the ring electrodes 120 are less than or equal to the diameters of the ring electrodes 120. In other embodiments, the lengths of the ring electrodes 120 are greater than the diameters of the ring electrodes 120. The distal-most ring electrode 120 may be a tip electrode (see, e.g., tip electrode 320a of FIG. 3E) which covers most, or all, of the distal tip of the lead.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S.

Patent Application Publication Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321, all of which are incorporated herein by reference.

In FIG. 1, the lead 100 is shown having a plurality of segmented electrodes 130. Any number of segmented electrodes 130 may be disposed on the lead body 110 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 110. A segmented electrode 130 typically extends only 75%, 67%, 60%, 50%, 40%, 33%, 25%, 20%, 17%, 15%, or less around the circumference of the lead.

The segmented electrodes 130 may be grouped into sets of segmented electrodes, where each set is disposed around a circumference of the lead 100 at a particular longitudinal portion of the lead 100. The lead 100 may have any number segmented electrodes 130 in a given set of segmented electrodes. The lead 100 may have one, two, three, four, five, six, seven, eight, or more segmented electrodes 130 in a given set. In at least some embodiments, each set of segmented electrodes 130 of the lead 100 contains the same number of segmented electrodes 130. The segmented electrodes 130 disposed on the lead 100 may include a different number of electrodes than at least one other set of segmented electrodes 130 disposed on the lead 100.

The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even all segmented electrodes disposed on the lead 100) may be identical in size and shape.

Each set of segmented electrodes 130 may be disposed around the circumference of the lead body 110 to form a substantially cylindrical shape around the lead body 110. The spacing between individual electrodes of a given set of the segmented electrodes may be the same, or different from, the spacing between individual electrodes of another set of segmented electrodes on the lead 100. In at least some embodiments, equal spaces, gaps or cutouts are disposed between each segmented electrode 130 around the circumference of the lead body 110. In other embodiments, the spaces, gaps or cutouts between the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body 110.

Conductor wires that attach to the ring electrodes 120 or segmented electrodes 130 extend along the lead body 110. These conductor wires may extend through the material of the lead 100 or along one or more lumens defined by the lead 100, or both. The conductor wires are presented at a connector (via terminals) for coupling of the electrodes 120, 130 to a control unit (not shown).

When the lead 100 includes both ring electrodes 120 and segmented electrodes 130, the ring electrodes 120 and the segmented electrodes 130 may be arranged in any suitable configuration. For example, when the lead 100 includes two sets of ring electrodes 120 and two sets of segmented electrodes 130, the ring electrodes 120 can flank the two sets of segmented electrodes 130 (see e.g., FIG. 1). Alternately, the two sets of ring electrodes 120 can be disposed proximal to the two sets of segmented electrodes 130 (see e.g., FIG. 3C), or the two sets of ring electrodes 120 can be disposed distal to the two sets of segmented electrodes 130 (see e.g., FIG. 3D). One of the ring electrodes can be a tip electrode (see, tip electrode 320a of FIGS. 3E and 3G). It will be understood that other configurations are possible as well (e.g., alternating ring and segmented electrodes, or the like).

By varying the location of the segmented electrodes 130, different coverage of the target neurons may be selected. For example, the electrode arrangement of FIG. 3C may be useful if the physician anticipates that the neural target will be closer to a distal tip of the lead body 110, while the electrode arrangement of FIG. 3D may be useful if the physician anticipates that the neural target will be closer to a proximal end of the lead body 110.

Figure 3F:
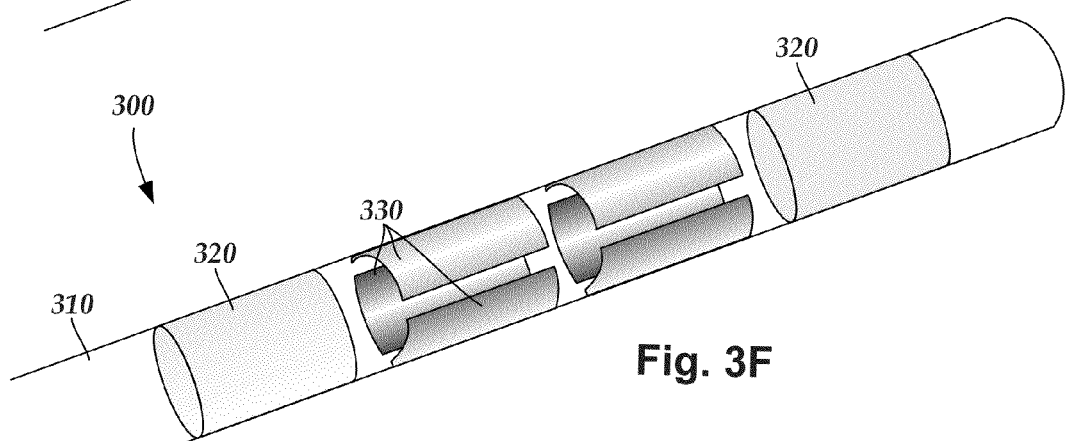
FIG. 3F is a perspective view of a sixth embodiment of a portion of a lead having a plurality of segmented electrodes, according to the invention.
Figure 3G:
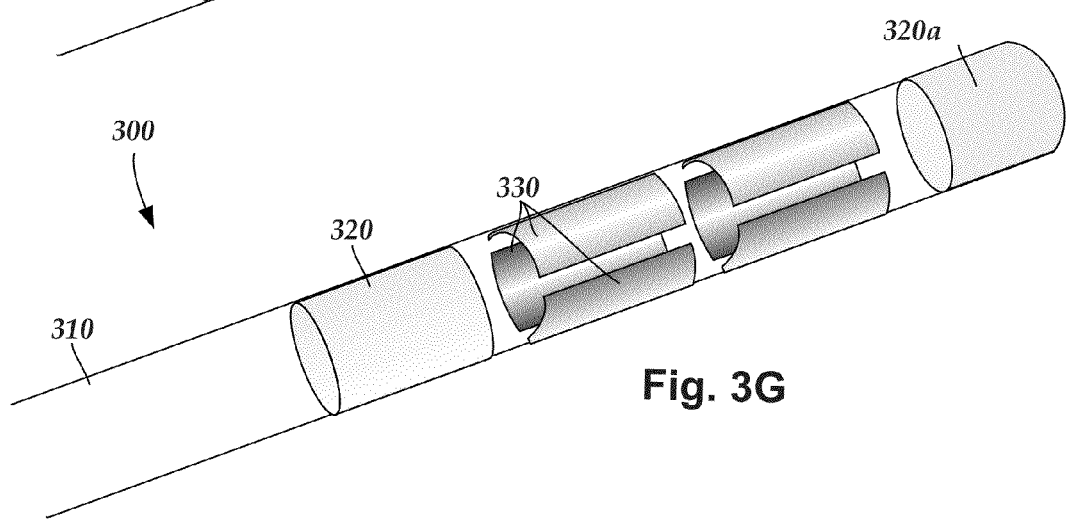
FIG. 3G is a perspective view of a seventh embodiment of a portion of a lead having a plurality of segmented electrodes, according to the invention.

Any combination of ring electrodes 120 and segmented electrodes 130 may be disposed on the lead 100. For example, the lead may include a first ring electrode 120, two sets of segmented electrodes; each set formed of four segmented electrodes 130, and a final ring electrode 120 at the end of the lead. This configuration may simply be referred to as a 1-4-4-1 (FIGS. 3A and 3E) configuration. It may be useful to refer to the electrodes with this shorthand notation. Thus, the embodiment of FIG. 3C may be referred to as a 1-1-4-4 configuration, while the embodiment of FIG. 3D may be referred to as a 4-4-1-1 configuration. The embodiments of FIGS. 3F and 3G can be referred to as a 1-3-3-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. The 1-3-3-1 electrode configuration of FIGS. 3F and 3G has two sets of segmented electrodes, each set containing three electrodes disposed around the circumference of the lead, flanked by two ring electrodes (FIG. 3F) or a ring electrode and a tip electrode (FIG. 3G). In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 2:
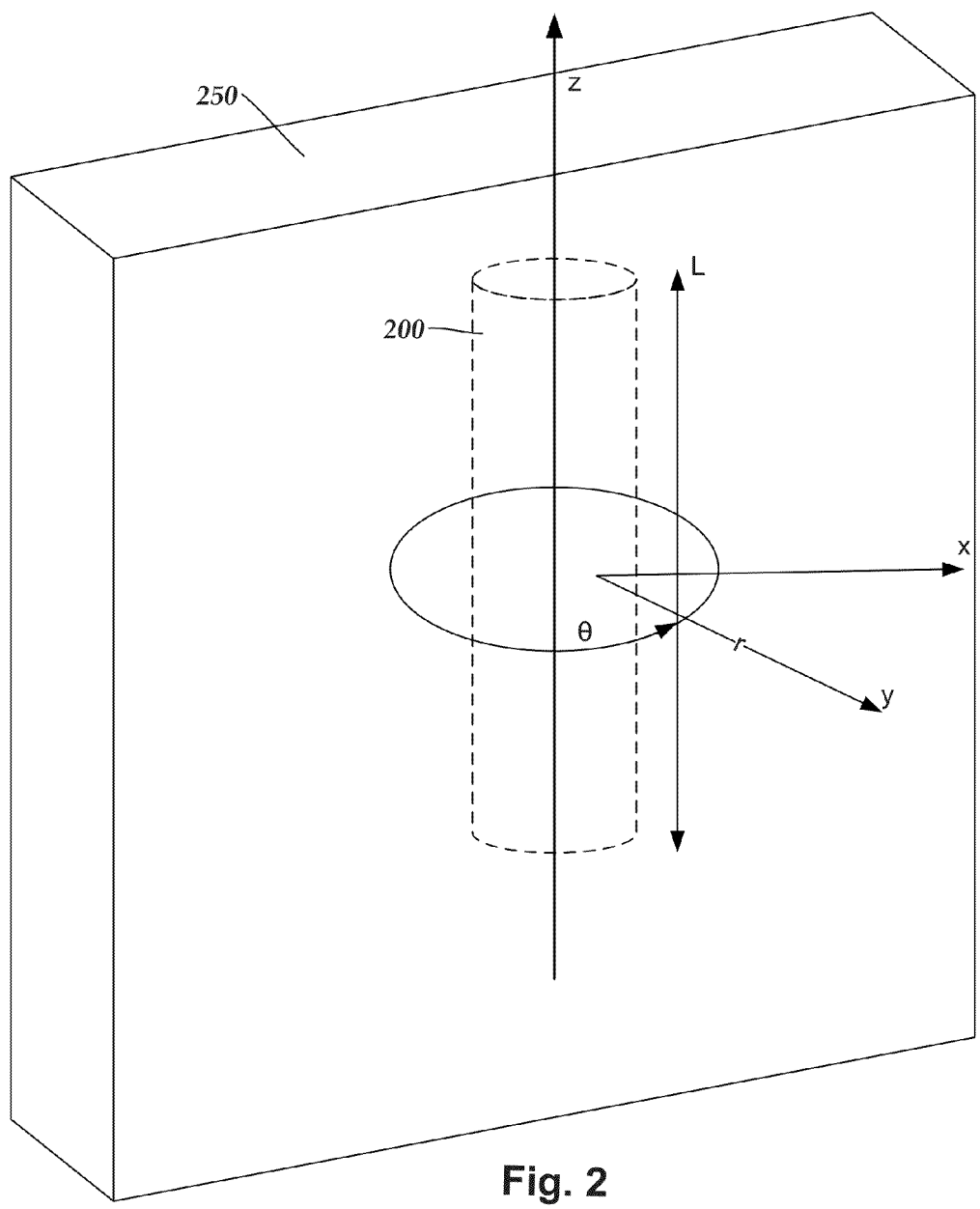
FIG. 2 is a schematic diagram of radial current steering along various electrode levels along the length of a lead, according to the invention.

FIG. 2 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 2, the centroid of stimulation can be shifted at each level along the length of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 230 in a set are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

Returning to FIG. 1, when the lead 100 includes a plurality of sets of segmented electrodes 130, it may be desirable to form the lead 100 such that corresponding electrodes of different sets of segmented electrodes 130 are radially aligned with one another along the length of the lead 100 (see e.g., the segmented electrodes 130 shown in FIG. 1). Radial alignment between corresponding electrodes of different sets of segmented electrodes 130 along the length of the lead 100 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 100 are radially aligned with one another and do not radially shift in relation to one another during manufacturing of the lead 100.

In other embodiments, individual electrodes in the two sets of segmented electrodes 130 are staggered (see, FIG. 3B) relative to one another along the length of the lead body 110. In some cases, the staggered positioning of corresponding electrodes of different sets of segmented electrodes along the length of the lead 100 may be designed for a specific application.

Segmented electrodes can be used to tailor the stimulation region so that, instead of stimulating tissue around the circumference of the lead as would be achieved using a ring electrode, the stimulation region can be directionally targeted. In some instances, it is desirable to target a parallelepiped (or slab) region 250 that contains the electrodes of the lead 200, as illustrated in FIG. 2. One arrangement for directing a stimulation field into a parallelepiped region uses segmented electrodes disposed on opposite sides of a lead.

FIGS. 3A-3G illustrate leads 300 with segmented electrodes 330, optional ring electrodes 320 or tip electrodes 320a, and a lead body 310. The sets of segmented electrodes 330 include either two (FIG. 3B), three (FIGS. 3F and 3G), or four (FIGS. 3A, 3C, and 3D) or any other number of segmented electrodes including, for example, five, six, or more.

Any other suitable arrangements of segmented electrodes can be used. As an example, arrangements in which segmented electrodes are arranged helically with respect to each other. One embodiment includes a double helix.

Sets of radially-disposed segmented electrodes can be formed from pre-electrodes. At least some conventional pre-electrodes include stimulation members coupled to one another by connecting material disposed along a periphery of the pre-electrodes. Formation of the segmented electrodes from such conventional pre-electrodes may include grinding down the connecting material disposed along the periphery of the pre-electrodes to physically separate the stimulation members from one another and form electrically-isolated segmented electrodes.

As herein described, a pre-electrode includes stimulation members coupled to one another via a central hub that can be removed during manufacture to physically separate the stimulation members from one another and form electrically-isolated segmented electrodes. In at least some embodiments each of the stimulation members is electrically-coupled to each of the remaining stimulation members solely via the central hub. In other words, in at least some embodiments the pre-electrode does not include connecting material that is disposed along a periphery of the pre-electrode and that couples together adjacent stimulation members. Thus, electrical isolation between the stimulation members may result solely by removal of the central hub.

The pre-electrodes described herein, as well as the segmented electrodes formed therefrom, may be formed of an electrical conductor such as a metal, alloy, conductive oxide, or any other suitable conductive material. In some embodiments, the pre-electrodes are formed of platinum, platinum-iridium, iridium, 616L stainless steel (or any other suitable stainless steel), tantalum, Nitinol, iridium rhodium, or a conductive polymer.

Figure 4A:
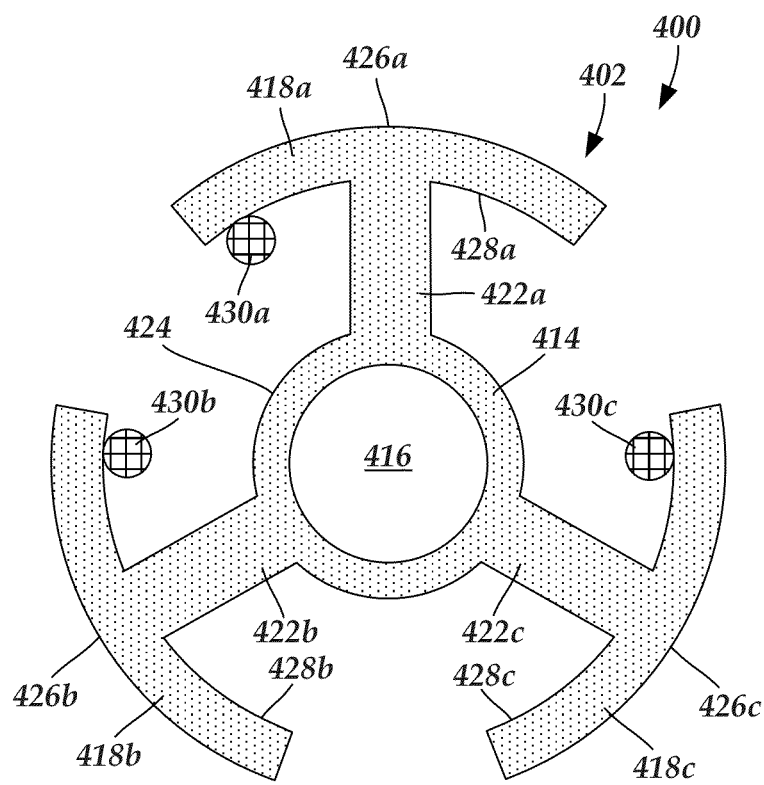
FIG. 4A is a schematic transverse cross-sectional view of one embodiment of a pre-electrode having three stimulation members each coupled to a central hub by a different one of three connector elements extending radially outward from the central hub, according to the invention.
Figure 4B:
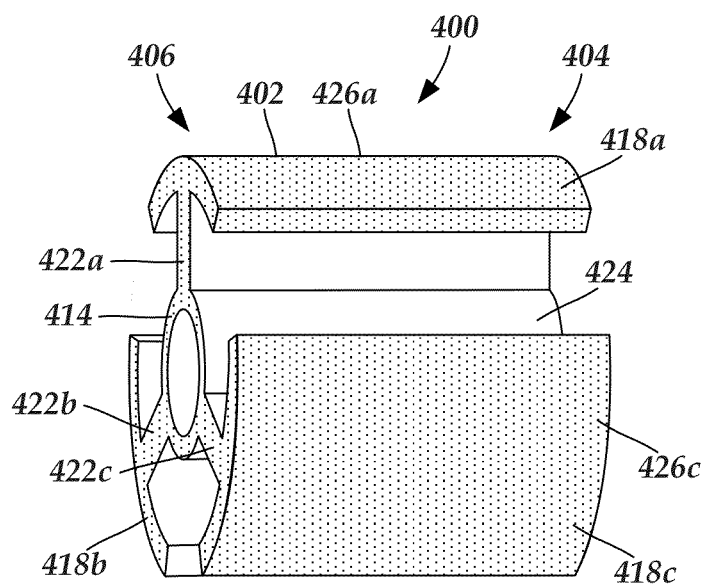
FIG. 4B is a schematic perspective view of one embodiment of the pre-electrode of FIG. 4A, according to the invention.

FIG. 4A schematically illustrates, in transverse cross-section, one embodiment of a pre-electrode 400 suitable for use in forming a set of radially-disposed segmented electrodes. FIG. 4B schematically illustrates one embodiment of the pre-electrode 400 in perspective view. The pre-electrode 400 includes a body 402 having a proximal end 404, a distal end 406, and a longitudinal length 408.

The body 402 includes a central hub 414 with a longitudinal surface 424. Stimulation members 418a, 418b, and 418c are coupled to the central hub 414 via connector elements 422a, 422b, and 422c, respectively, extending radially from the longitudinal surface 424 of the central hub 414. In FIGS. 4A and 4B (and in other figures) the stimulation members 418a, 418b, and 418c are each shown coupled to the central hub 414 by a single connector element 422a, 422b, or 422c. In at least some embodiments, at least one of the stimulation members 418a, 418b, and 418c is coupled to the central hub 414 by multiple connector elements 422a, 422b, or 422c.

The central hub 414 can be any suitable shape and shape. In FIGS. 4A and 4B, the central hub 414 is shown as being tube-shaped with a hub aperture 416. It may be beneficial to form the central hub 414 as tube-shaped, or substantially tube-shaped, so that when electrically-nonconductive material is disposed about the longitudinal surface 424 of the central hub 414 (see e.g., FIG. 9A) and the central hub 414 is removed (see e.g., FIG. 9B), the central lumen formed at the location formerly occupied by the central hub 414 is similar in size and shape to the axially-disposed stylet lumen (not shown) that extends along the longitudinal length of the lead and that receives the stylet (140 in FIG. 1) during implantation of the lead.

The connector elements 422a, 422b, and 422c can extend along the entire longitudinal length 408 of the body 402, or only a portion of the longitudinal length 408. In at least some embodiments, the connector elements 422a, 422b, and 422c are coupled to the longitudinal surface 424 of the central hub 414 such that the connector elements 422a, 422b, and 422c are equally spaced around a circumference of the central hub 414. For example, in FIG. 4A three connector elements 422a, 422b, and 422c are shown as each being 120° apart from the remaining two connector elements around a circumference of the central hub 414. As another example, in FIG. 8 four connector elements 822a, 822b, 822c, and 822d are shown as each being 90° apart from the adjacent two connector elements around a circumference of the central hub 814.

The body 402 of the pre-electrode 400 can be any suitable shape. In at least some embodiments, the body 402 is substantially cylindrical, with the stimulation members 418a, 418b, and 418c forming an outer periphery of the body 402. In some embodiments, the outer surfaces 426a, 426b, and 426c of the stimulation members 418a, 418b, and 418c form the outer surfaces of the segmented electrodes (see e.g., FIG. 9C) during operation of the segmented electrodes. In other embodiments, the outer surfaces 426a, 426b, and 426c of the stimulation members 418a, 418b, and 418c are ground down prior to operation as electrically-isolated segmented electrodes.

The body 402 of the pre-electrode 400 can be any suitable size. In at least some embodiments, the body 402 has a diameter that is equal, or substantially equal, to a diameter of the distal end portion of the lead (see e.g., 110 in FIG. 1) onto which the pre-electrode is to be disposed.

The stimulation members 418a, 418b, and 418c can extend along the entire longitudinal length 408 of the body 402, or only a portion of the longitudinal length 408. The stimulation members 418a, 418b, and 418c each include outer surfaces 426a, 426b, and 426c, respectively, and inner surfaces 428a, 428b, and 428c, respectively. In at least some embodiments, the connector elements 422a, 422b, and 422c couple to the stimulation members 418a, 418b, and 418c, respectively, along the inner surfaces 428a, 428b, and 428c of the stimulation members 418a, 418b, and 418c, respectively.

The outer surfaces 426a, 426b, and 426c of the stimulation members 418a, 418b, and 418c can be any suitable shape. In at least some embodiments, the stimulation members 418a, 418b, and 418c are arcuate with the outer surfaces 426a, 426b, and 426c being convex and the inner surfaces 428a, 428b, and 428c being concave. In at least some embodiments, the stimulation members 418a, 418b, and 418c are arced such that the outer surfaces 426a, 426b, and 426c are similarly arced as a transverse cross-section of the lead (see e.g., 952 in FIGS. 9B and 9C) onto which the pre-electrode is to be disposed.

Stimulation energy passed through the segmented electrodes (see e.g., 918a, 918b, and 918c of FIGS. 9B and 9C) formed from the pre-electrode 400 is typically provided to the segmented electrodes via conductors, such as conductors 430a, 430b, and 430c. The conductors 430a, 430b, and 430c can be coupled either: to the stimulation members 418a, 418b, and 418c of the pre-electrode 400; or to the segmented electrodes (see e.g., 918a, 918b, and 918c of FIGS. 9B and 9C) formed from the stimulation members 418a, 418b, and 418c. It may be advantageous to couple the conductors 430a, 430b, and 430c to the stimulation members 418a, 418b, and 418c prior to disposing the electrically-nonconductive material around the central hub 414 to obviate subsequent removal of portions of the electrically-nonconductive material to access the stimulation members 418a, 418b, and 418c (or the segmented electrodes formed therefrom).

In FIG. 4A, the conductors 430a, 430b, and 430c are shown coupled to the inner surfaces 428a, 428b, and 428c of the stimulation members 418a, 418b, and 418c, respectively. Alternately or additionally, one or more of the conductors 430a, 430b, and 430c can be coupled to one or more of the connector elements 422a, 422b, and 422c, respectively, in lieu of or in addition to the inner surfaces 428a, 428b, and 428c of the stimulation members 418a, 418b, and 418c, respectively.

Figure 5:
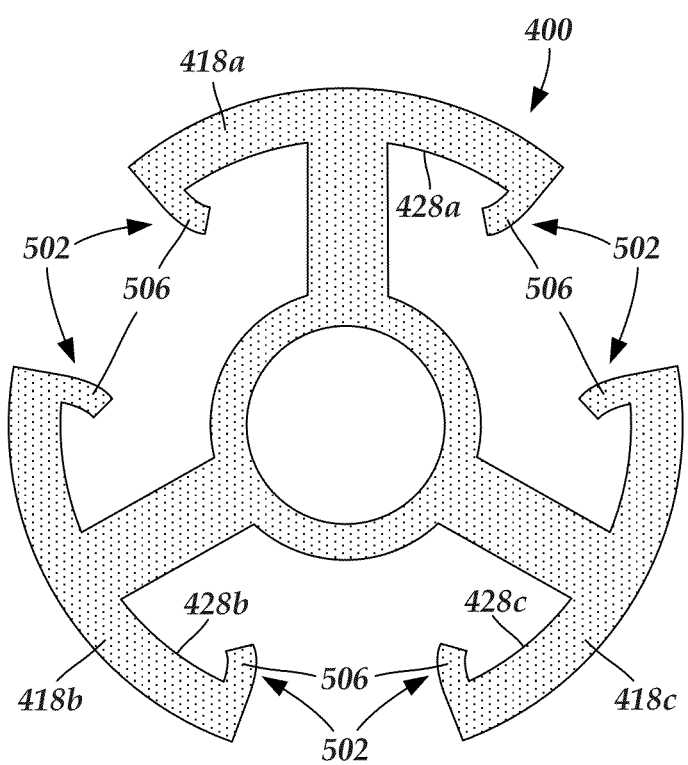
FIG. 5 is a schematic transverse cross-sectional view of one embodiment of the pre-electrode of FIG. 4A having stimulation members coupled to a central hub by connector elements extending radially outward from the central hub, the pre-electrode including lead-retention features formed as barbs disposed along inner surfaces of the stimulation members, according to the invention.
Figure 6:
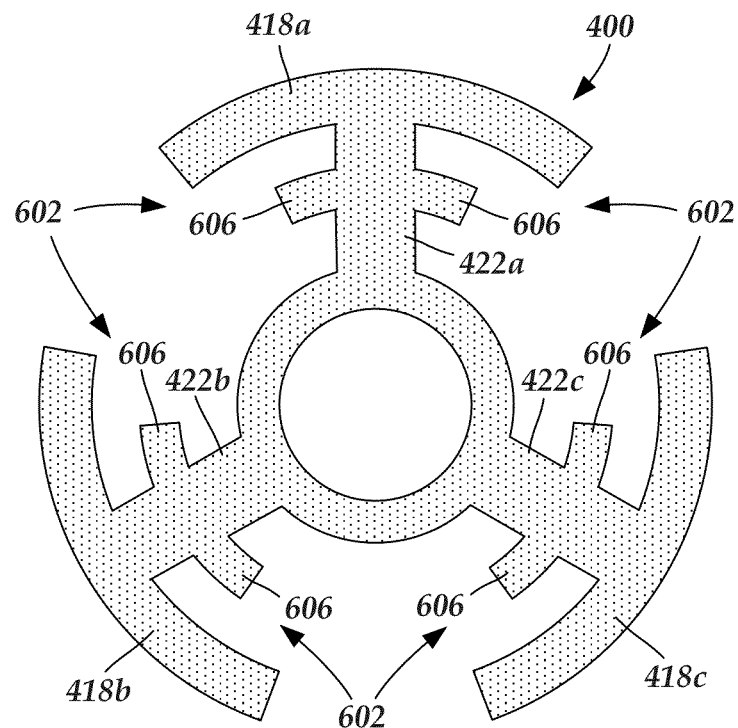
FIG. 6 is a schematic transverse cross-sectional view of yet another embodiment of the pre-electrode of FIG. 4A having stimulation members coupled to a central hub by connector elements extending radially outward from the central hub, the pre-electrode including lead-retention features formed as barbs disposed along the connector elements, according to the invention.
Figure 7:
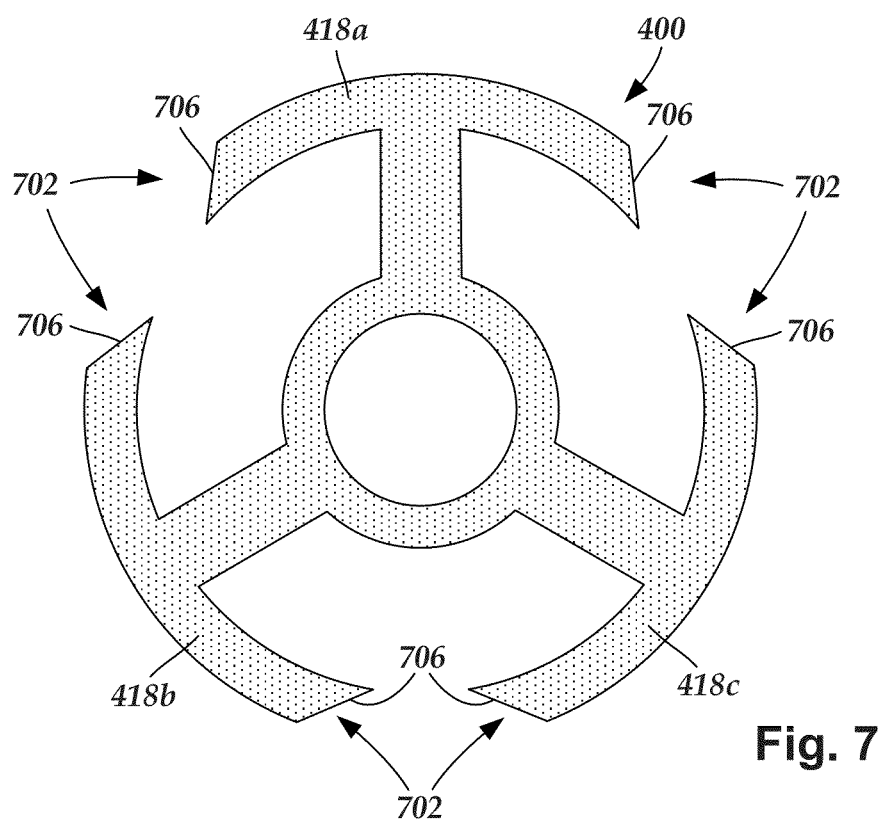
FIG. 7 is a schematic transverse cross-sectional view of another embodiment of the pre-electrode of FIG. 4A having stimulation members coupled to a central hub by connector elements extending radially outward from the central hub, the pre-electrode including lead-retention features formed as undercuts disposed along the stimulation members, according to the invention.

Turning to FIGS. 5-7, during the manufacturing process an electrically-nonconductive material is disposed about the longitudinal surface of the central hub. The electrically-nonconductive material extends radially-outward from the central hub to the stimulation members such that the inner surfaces of the stimulation members are encased in the electrically-nonconductive material. In some embodiments, the electrically-nonconductive material extends radially-outward from the central hub to the stimulation members such the outer (longitudinal) surface of the electrically-nonconductive material is flush with the outer surfaces of the stimulation members.

The electrically-nonconductive material can be disposed over the longitudinal surface of the central hub in any suitable manner including, for example, injection molding, re-flowing polymeric material, or the like. The pre-electrode may, optionally, include one or more lead-retention features disposed along one or more of the stimulation members 418a, 418b, and 418c, one or more of the connector elements 422a, 422b, and 422c, or both. The one or more lead-retention features may be used to promote adhesion of the electrically-nonconductive material to the pre-electrode (and to the segmented electrodes formed therefrom). Additionally, once the segmented electrodes are formed from the pre-electrode, the one or more lead-retention features, in addition to promoting adhesion of the segmented electrodes to the electrically-nonconductive material, may also facilitate maintaining relative positioning and the physical separation (and electrical isolation) between the segmented electrodes.

FIG. 5 schematically illustrates, in transverse cross-section, one embodiment of lead-retention features 502 disposed along the pre-electrode 400. In FIG. 5, the lead-retention features 502 are formed as barbs 506 extending from the inner surfaces 428a, 428b, and 428c of the stimulation members 418a, 418b, and 418c, respectively. The barbs 506 can be disposed along any suitable portion of the inner surfaces 428a, 428b, and 428c of the stimulation members 418a, 418b, and 418c. In FIG. 5, the barbs 506 are shown extending from opposing ends of the inner surfaces 428a, 428b, and 428c of the stimulation members 418a, 418b, and 418c. The barbs 506 can be formed from either the same material or from different material as the stimulation members 418a, 418b, and 418c.

Any suitable number of barbs 506 can be disposed on the pre-electrode 400 including, for example, one, two, three, four, five, six, seven, eight, nine, ten, eleven, twelve, fifteen, or more barbs 506. In at least some embodiments, at least one barb 506 is disposed on each of the stimulation members 418a, 418b, and 418c. In at least some embodiments, at least two barbs 506 are disposed on each of the stimulation members 418a, 418b, and 418c. In at least some embodiments, an equal number of barbs 506 are disposed on each of the stimulation members 418a, 418b, and 418c.

FIG. 6 schematically illustrates, in transverse cross-section, another embodiment of lead-retention features 602 disposed along the pre-electrode 400. In FIG. 6, the lead-retention features 602 are formed as barbs 606 extending from the connector elements 422a, 422b, and 422c. The barbs 606 can be disposed along any suitable portion of the connector elements 422a, 422b, and 422c. In FIG. 6, the barbs 606 are shown extending from opposing sides of the connector elements 422a, 422b, and 422c along a length of the connector elements 422a, 422b, and 422c. The barbs 606 can be formed from either the same material or from different material as the connector elements 422a, 422b, and 422c.

Any suitable number of barbs 606 can be disposed on the pre-electrode 400 including, for example, one, two, three, four, five, six, seven, eight, nine, ten, eleven, twelve, fifteen, or more barbs 606. In at least some embodiments, at least one barb 606 is disposed on each of the connector elements 422a, 422b, and 422c. In at least some embodiments, at least two barbs 606 are disposed on each of the connector elements 422a, 422b, and 422c. In at least some embodiments, at least one barb 606 is disposed on each side of each of the connector elements 422a, 422b, and 422c. In at least some embodiments, an equal number of barbs 606 are disposed on each of the connector elements 422a, 422b, and 422c.

FIG. 7 schematically illustrates, in transverse cross-section, one embodiment of lead-retention features 702 disposed along the pre-electrode 400. In FIG. 7, the lead-retention features 702 are formed as undercuts 706 formed along at least one longitudinal edge of the stimulation members 418a, 418b, and 418c. In FIG. 7, the undercuts 706 are shown formed along opposing ends of the stimulation members 418a, 418b, and 418c.

Any suitable number of undercuts 706 can be disposed on the pre-electrode 400 including, for example, one, two, three, four, five, six, or more undercuts 706. In at least some embodiments, at least one undercut 706 is disposed on each of the stimulation members 418a, 418b, and 418c. In at least some embodiments, at least two undercuts 706 are disposed on each of the stimulation members 418a, 418b, and 418c. In at least some embodiments, an equal number of undercuts 706 are disposed on each of the stimulation members 418a, 418b, and 418c.

It will be understood that the lead-retention features shown in FIGS. 5-7 (and in other figures) can be used in any suitable combination. For example, a pre-electrode may have undercuts and barbs (either disposed along one or more of the stimulation members or disposed along one or more of the connector elements). As another example, a pre-electrode may have no undercuts but may have barbs disposed along both the stimulation members and the one or more of the connector elements.

Figure 8:
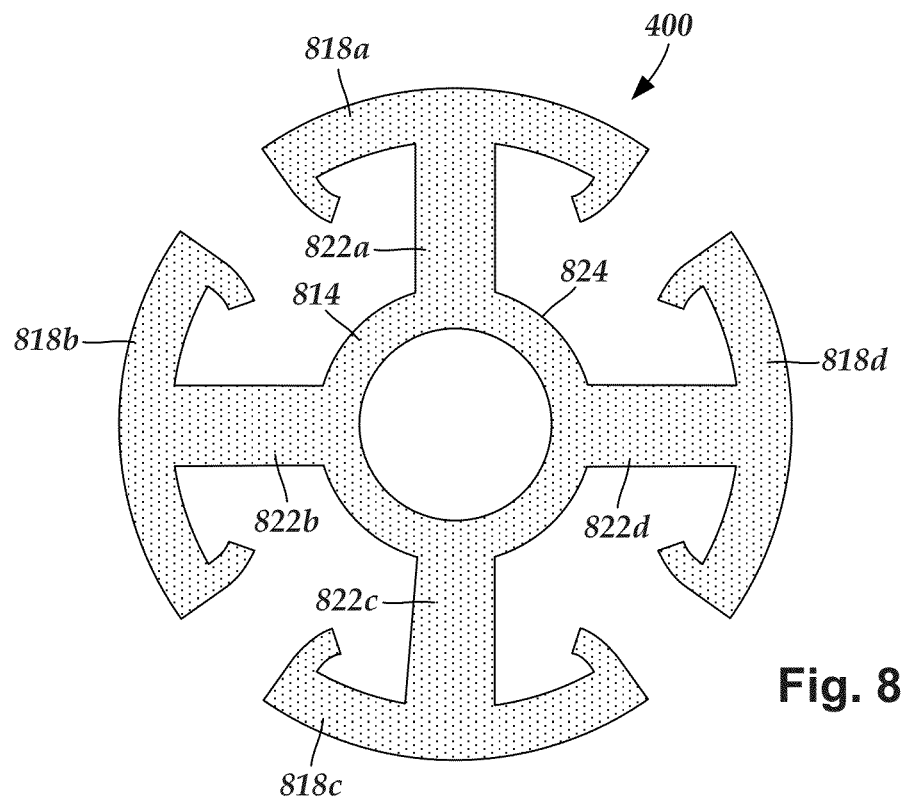
FIG. 8 is a schematic transverse cross-sectional view of yet another embodiment of the pre-electrode of FIG. 4A, the pre-electrode having four stimulation members each coupled to a central hub by a different one of four connector elements extending radially outward from the central hub, according to the invention.

In FIGS. 4A-7 (and in other figures), the pre-electrode is shown having three stimulation members. It will be recognized that the pre-electrode may include any suitable number of stimulation members including, for example, two, three, four, five, six, seven, eight, or more stimulation members. FIG. 8 schematically illustrates, in transverse cross-section, one embodiment of the pre-electrode 400 with a body 802 having four stimulation members 818a, 818b, 818c, and 818d. The body 802 includes a central hub 814 with a longitudinal surface 824. The stimulation members 818a, 818b, 818c, and 818d are coupled to the central hub 814 via connector elements 822a, 822b, 822c, and 822d, respectively, extending radially from the longitudinal surface 824 of the central hub 814. The stimulation members 818a, 818b, 818c, and 818d are each shown coupled to the central hub 414 by a single connector element 822a, 822b, 822c, and 822d. In at least some embodiments, at least one of the stimulation members 818a, 818b, 818c, and 818d is coupled to the central hub 814 by multiple connector elements 822a, 822b, 822c, and 822d.

Figure 9A:
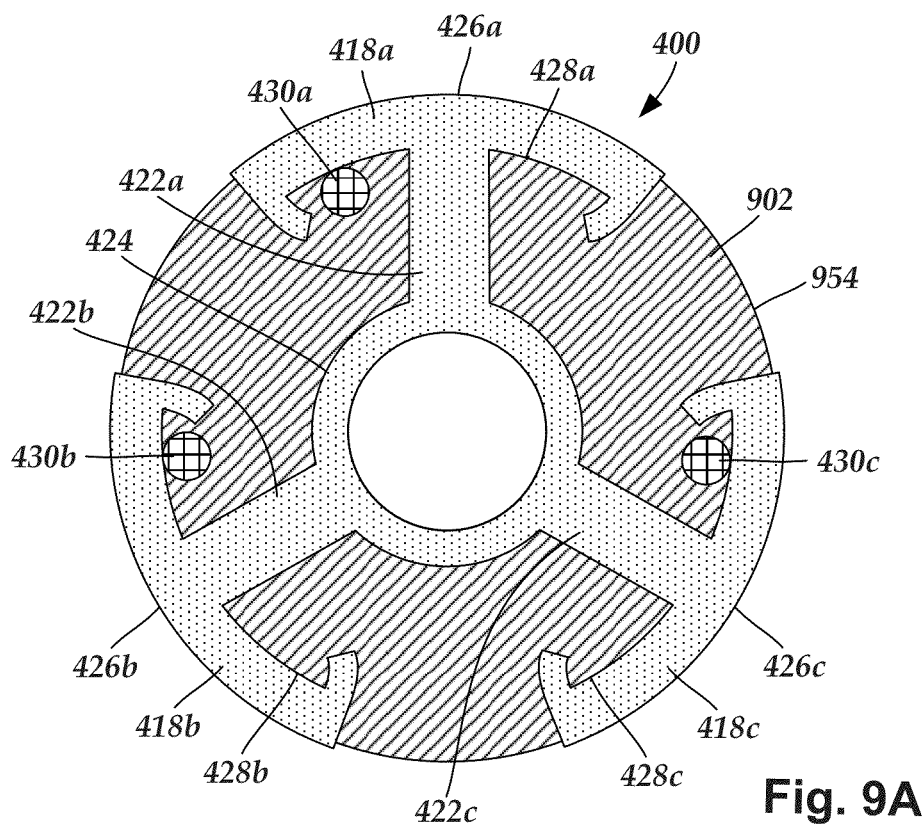
FIG. 9A is a schematic transverse cross-sectional view of one embodiment of a distal end portion of a lead, the lead including the pre-electrode of FIG. 5 and electrically-nonconductive material disposed radially about a central hub of the pre-electrode and between stimulation members of the pre-electrode, according to the invention.
Figure 9B:
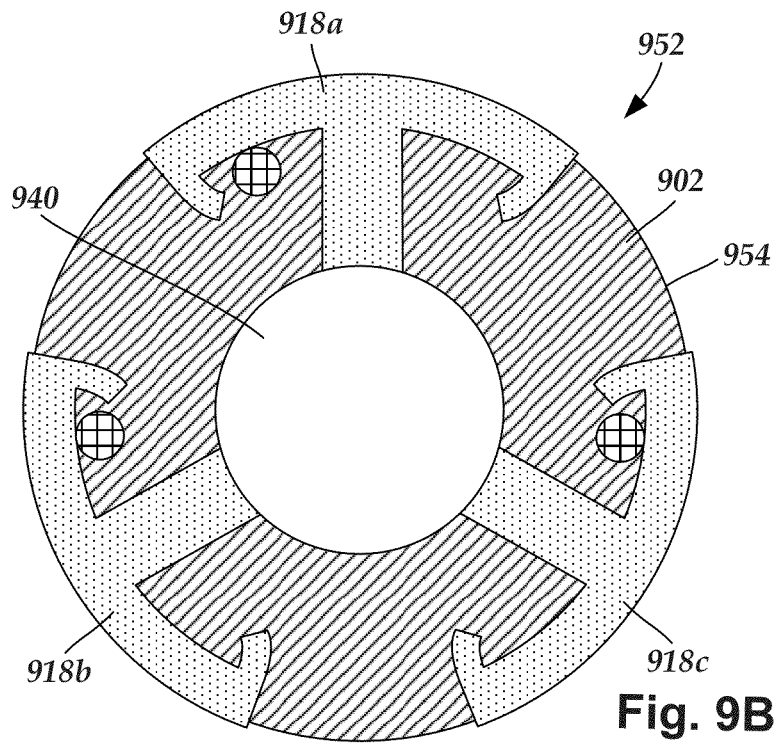
FIG. 9B is a schematic transverse cross-sectional view of one embodiment of a distal end portion of the lead of FIG. 9A, the lead including the electrically-nonconductive material of FIG. 9A and segmented electrodes formed from the pre-electrode of FIG. 9A, the segmented electrodes formed by removing a central hub of the pre-electrode to electrically isolate stimulation portions of the pre-electrode to form the segmented electrodes, the removal of the central hub forming a central lumen along the lead with portions of the segmented electrodes open to the central lumen.
Figure 9C:
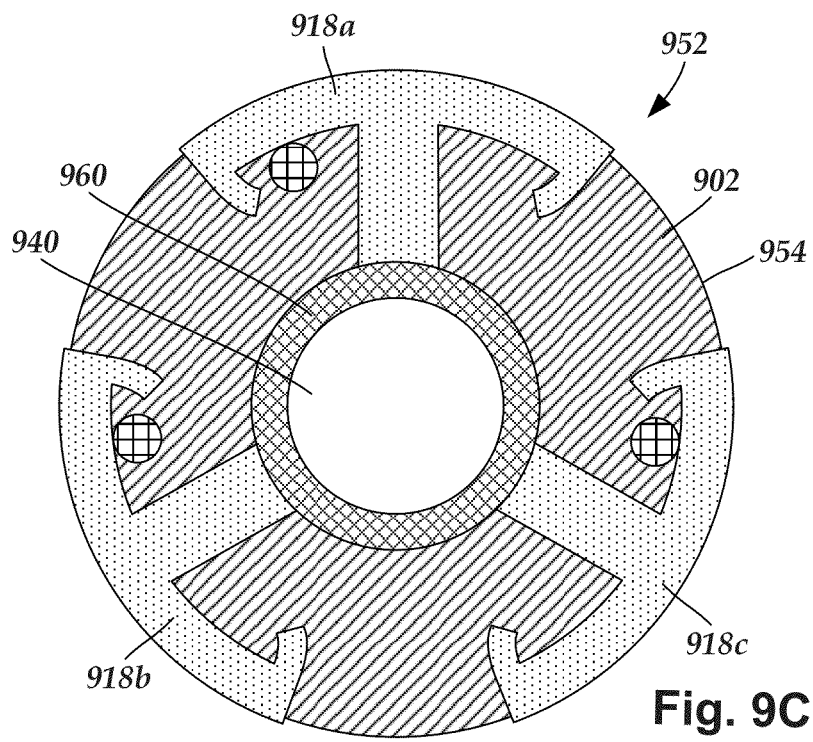
FIG. 9C is a schematic transverse cross-sectional view of one embodiment of the lead of FIG. 9B, the lead including the central lumen of FIG. 9B, the electrically-nonconductive material of FIG. 9B, the segmented electrodes of FIG. 9B, the central lumen of FIG. 9B, and insulating material disposed along at least a portion of the longitudinal walls of the central lumen to electrically isolate the segmented electrodes from the central lumen, according to the invention.

Turning to FIGS. 9A-9C, the pre-electrodes are typically disposed along a distal end portion of the lead and the central hubs removed to electrically-isolate each of the stimulation members (and their attached connector elements) from one another, thereby forming segmented electrodes. The pre-electrode of FIG. 5 is shown in each of FIGS. 9A-9C. It will be understood that the techniques for disposing pre-electrodes on leads and for electrically-isolating the stimulation members (and their attached connector elements) to form segmented electrodes are applicable for each of the pre-electrodes described herein.

FIG. 9A schematically illustrates, in transverse cross-section, one embodiment of electrically-nonconductive material 902 disposed radially about the central hub 414 of the pre-electrode 400. The electrically-nonconductive material 902 encases the longitudinal surfaces 424 of the central hub 414 and the connector elements 422a, 422b, and 422c. Additionally, the electrically-nonconductive material 902 abuts the inner surfaces 428a, 428b, and 428c of the stimulation members 418a, 418b, and 418c, respectively. In at least some embodiments, the electrically-nonconductive material 902 is disposed about the central hub 414 so that the outer surfaces 426a, 426b, and 426c of the stimulation members 418a, 418b, and 418c, respectively, are flush, or approximately flush, with longitudinal surface 954 of the electrically-nonconductive material 902.

Any suitable biocompatible, electrically-nonconductive material may be used. In at least some embodiments, the electrically-nonconductive material is a polymeric material. In at least some embodiments, the electrically-nonconductive material is the same material (or similar material) to the material used to form the lead body (e.g., polyurethane, silicone, adhesive, or the like or combinations thereof). The electrically-nonconductive material 902 can be disposed over the longitudinal surface 424 of the central hub 414 in any suitable manner including, for example, injection molding, re-flowing, or the like.

FIG. 9A shows the conductors 430a, 430b, and 430c coupled to stimulation members 418a, 418b, and 418c, respectively. As mentioned above, the conductors 430a, 430b, and 430c can be coupled to stimulation members 418a, 418b, and 418c (or to attached connector elements), either before or after the electrically-nonconductive material is disposed around the central hub 414.

The pre-electrode can be attached to the end of a lead body in any suitable manner including, for example, re-flowing the electrically-nonconductive material, re-flowing the material of the lead body (or both), re-flowing both the electrically-nonconductive material and the material of the lead body, applying an adhesive, or the like or combinations thereof. Alternately, the lead body can be formed simultaneously with the formation of the segmented electrodes so that the lead body and the electrically-nonconductive material disposed about the central hub are formed as a single structure. In at least some embodiments, the lead may include multiple sets of segmented electrodes (or ring or tip electrodes). In which case, multiple pre-electrodes may be arranged in a desired axial configuration with electrically-nonconductive material disposed axially between axially-adjacent pre-electrodes (or ring or tip electrodes).

Once the electrically-nonconductive material is disposed about the central hub, the central hub may be removed. Once the central hub of the pre-electrode is removed, the remaining electrically-isolated stimulation members, and their corresponding connector elements, are referred to as segmented electrodes. The removal of the central hub may additionally remove at least a portion of at least one of the connector elements.

FIG. 9B schematically illustrates, in transverse cross-section, one embodiment of a distal end portion of a lead 952. The lead 952 includes the electrically-nonconductive material 902 and segmented electrodes 918a, 918b, and 918c formed from the pre-electrode 400 by the removal of the central hub 414 of the pre-electrode 400. Removal of the central hub 414 causes a central lumen 940 to be formed in the electrically-nonconductive material 902 at the location along the lead 952 where the central hub 414 was positioned prior to being removed.

Removal of the central hub 414 can be performed in any suitable manner. In at least some embodiments, the central hub 414 is bored out (e.g., drilled out, or the like). For example, a drill may be passed through a portion of the lead 952 that includes the central hub 414. In at least some embodiments, the drill is passed through a distal tip of the lead 952 and extended through the longitudinal length (408 in FIG. 4B) of the pre-electrode. Boring out the central hub 414 in such a manner may form the central lumen 940 along the distal end portion of the lead, in addition to the space formerly occupied by the central hub 414. In at least some embodiments where the drill is passed through the distal tip of the lead, the distal tip may be subsequently capped or a tip electrode may subsequently be disposed along the distal tip.

In at least some embodiments, the lead body includes a stylet lumen for receiving the stylet (140 in FIG. 1). The pre-electrode may be disposed on the lead body such that the central hub 414 is axially aligned with, and open to, the stylet lumen. Such an arrangement may enable the stylet to be introduced into the central lumen 940 during implantation. When the central hub is removed via a drill, and when the central hub is axially aligned with, and open to, the stylet lumen the drill may, in at least some embodiments, be passed along at least a portion of the stylet lumen.

As shown in FIG. 9B, when the central hub is removed from the pre-electrode one or more portions of the segmented electrodes (e.g., one or more connector-element portions of the segmented electrodes) may be physically exposed to the central lumen 940. It may be desirable to avoid having portions of the segmented electrode be physically exposed to the central lumen 940 to prevent potential undesired short-circuiting caused by, for example, bodily fluids seeping into the central lumen over time during operation). In at least some embodiments, an insulating material is disposed between the body of the lead and the central lumen 940 at the distal end portion of the lead body. The insulating material is electrically-nonconductive and functions to electrically-isolate the segmented electrodes from the central lumen 940.

FIG. 9C schematically illustrates, in transverse cross-section, one embodiment of the distal end portion of the lead 952. The lead 952 includes the central lumen 940 and segmented electrodes 918a, 918b, and 918c formed from the pre-electrode 400. The segmented electrodes 918a, 918b, and 918c shown in FIG. 9C include the stimulation members 418a, 418b, and 418c, and the attached connector elements 422a, 422b, and 422c of the pre-electrode 400. The stimulation members 418a, 418b, and 418c include outer surfaces 426a, 426b, and 426c and opposing inner surfaces 428a, 428b, and 428c (as shown in FIG. 9A).

The outer surfaces 426a, 426b, and 426c of the segmented electrodes 918a, 918b, and 918c, respectively, are exposed along a longitudinal surface 954 of the electrically-nonconductive material 902. In at least some embodiments, the outer surfaces 426a, 426b, and 426c of the segmented electrodes 918a, 918b, and 918c and/or the longitudinal surface 954 of the electrically-nonconductive material 902 may be ground down so that the outer surfaces 426a, 426b, and 426c of the segmented electrodes 918a, 918b, and 918c and the longitudinal surface 954 of the electrically-nonconductive material 902 are flush with one another.

In at least some embodiments, after the central hub of the pre-electrode is removed the connector-element portions of the segmented electrodes each extend along at least 20%, 30%, 40%, 50%, 60%, 70%, or more of a radius of the lead. As mentioned above, when the central hub is removed the connector-element portions of the segmented electrodes may be physically exposed to the central lumen 940.

In at least some embodiments, insulating material 960 is disposed along at least a portion of the longitudinal walls of the central lumen 940 to electrically-isolate the segmented electrodes 918a, 918b, and 918c from the central lumen 940. In at least some embodiments, when the insulating material 960 is disposed along at least a portion of the longitudinal walls of the central lumen 940 the connector-element portions of the segmented electrodes 918a, 918b, and 918c physically abut the insulating material 960.

The insulating material 960 can be formed from any suitable electrically-nonconductive material including, for example, polyurethane, silicone, adhesive, or the like or combinations thereof. In at least some embodiments, the insulating material 960 is formed from a different material from the electrically-nonconductive material 902. In at least some embodiments, the insulating material 960 is formed from a different material from the electrically-nonconductive material used to form the lead body. In at least some embodiments, the insulating material 960 is formed from a different material from the electrically-nonconductive material 902 or the material used to form the lead body.

The insulating material 960 can be applied to the longitudinal walls of the central lumen 940 using any suitable technique. In at least some embodiment, the insulating material 960 is formed as a liner that is inserted into the central lumen 940 and re-flowed with the walls of the central lumen 940. Other techniques for applying the insulating material 960 may include, for example, injection molding, chemical vapor deposition, or the like.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A pre-electrode for a stimulation lead, the pre-electrode comprising:
   a substantially-cylindrical pre-electrode body having a proximal end and a distal end, the pre-electrode body comprising
   an electrically-conductive central huh having a longitudinal surface,
   a plurality of connector elements extending radially outward from the longitudinal surface of the central hub, the plurality of connector elements each having a medial end coupled to the central huh and an opposing lateral end, and
   a plurality of stimulation members each having an inner surface and an outer surface, the inner surface of each of the plurality of stimulation members coupled to the lateral end of at least one of the plurality of connector elements such that each of the plurality of stimulation members is electrically-coupled to each of remaining stimulation members of the plurality of stimulation members solely via the central hub, and wherein the plurality of stimulation members are arranged circumferentially in a single circle around the central hub.

2. The pre-electrode of claim 1, wherein the central hub is tube-shaped.

3. The pre-electrode of claim 1, wherein the inner surface of each of the plurality of stimulation members is coupled to the lateral end of exactly one connector element of the plurality of connector elements.

4. A method of making a stimulation lead, the method comprising forming at least one pre-electrode of claim 1 and disposing the at least one pre-electrode along a distal end portion of a lead body;

electrically-coupling at least one conductor of a plurality of conductors extending from a plurality of terminals disposed along a proximal end portion of the lead body to each of the plurality of stimulation members;

disposing electrically-nonconductive material around longitudinal surfaces of the central hub with the electrically-nonconductive material abutting inner surfaces of the plurality of stimulation members; and removing the central hub from the pre-electrode body to electrically isolate each of the plurality of stimulation members from one another, thereby transforming the plurality of stimulation members into a plurality of electrically-isolated segmented electrodes disposed along the electrically-nonconductive material.

5. The method of claim 4, wherein disposing the at least one pre-electrode along a distal end portion of a lead body comprises disposing along the distal end portion of the lead body the at least one pre-electrode that comprises exactly three electrically-conductive stimulation members.

6. The method of claim 4, wherein removing the central hub to electrically isolate each of the plurality of stimulation members from one another comprises passing a drill along a portion of the lead body that includes the central hub to remove the central hub and sever connections between the plurality of connector elements, the passing of the drill forming a central lumen along at least a portion of the lead body.

7. The method of claim 4, further comprising disposing insulating material along walls of the central lumen to electrically isolate the segmented electrodes from the central lumen.

8. The method of claim 7, wherein disposing insulating material along walls of the central lumen comprises re-flowing electrically-nonconductive tubing along the walls of the central lumen.

9. The method of claim 7, wherein disposing insulating material along walls of the central lumen comprises depositing electrically-nonconductive material using chemical vapor deposition along the walls of the central lumen.

10. The method of claim 7, wherein disposing insulating material along walls of the central lumen comprises injection molding electrically-nonconductive material along the walls of the central lumen.

11. The method of claim 4, wherein disposing electrically-nonconductive material around longitudinal surfaces of the central huh with the electrically-nonconductive material abutting inner surfaces of the plurality of stimulation members comprises disposing electrically-nonconductive material around longitudinal surfaces of the central huh with the electrically-nonconductive material flush with outer surfaces of the plurality of stimulation members.

\* \* \* \* \*